US010428715B2

(12) United States Patent
Otsuki

(10) Patent No.: US 10,428,715 B2

(45) Date of Patent: Oct. 1, 2019

(54) EXHAUST GAS ANALYZING SYSTEM AND PUMPING DEVICE

(71) Applicant: HORIBA, Ltd., Kyoto (JP)

(72) Inventor: Yoshinori Otsuki, Kyoto (JP)

(73) Assignee: HORIBA, LTD., Kyoto (JP)

( * ) Notice: Subject to any disclaimer, the term of this patent is extended or adjusted under 35 U.S.C. 154(b) by 471 days.

(21) Appl. No.: 14/923,834

(22) Filed: Oct. 27, 2015

(65) Prior Publication Data

US 2016/0115850 A1 Apr. 28, 2016

(30) Foreign Application Priority Data

Oct. 27, 2014 (JP) ................................ 2014-218275

(51) Int. Cl.

*F01N 1/00* (2006.01)
*F01N 11/00* (2006.01)
*F01N 3/021* (2006.01)
*F04B 45/04* (2006.01)
*G01M 15/10* (2006.01)
*G01N 1/22* (2006.01)
*G01N 1/24* (2006.01)

(52) U.S. Cl.

CPC ............ *F01N 11/002* (2013.01); *F01N 3/021* (2013.01); *F04B 45/04* (2013.01); *G01M 15/102* (2013.01); *G01N 1/2252* (2013.01); *F01N 2550/04* (2013.01); *G01N 1/24* (2013.01); *G01N 2001/2255* (2013.01)

(58) Field of Classification Search

CPC ........ F01N 11/002; F01N 3/021; F04B 45/04; G01M 15/102; G01N 1/2252

USPC ........................................................... 60/276

See application file for complete search history.

(56) References Cited

U.S. PATENT DOCUMENTS 8,505,276 B2 8/2013 Nakamura
2011/0120096 A1 5/2011 Nakamura
2012/0266687 A1 10/2012 Takahashi
2012/0266887 A1 10/2012 Takahashi
2012/0304737 A1 12/2012 Guenther et al.

FOREIGN PATENT DOCUMENTS

CN 102066900 A 5/2011
CN 202215940 U 5/2012
CN 102536847 A 7/2012
CN 102652256 A 8/2012

(Continued)

OTHER PUBLICATIONS

EESR dated Mar. 30, 2016 issued for European Patent Application No. 15 190 973.6, 7 pgs.

(Continued)

*Primary Examiner* — Jason D Shanske

(74) *Attorney, Agent, or Firm* — Brooks Kushman P.C.

(57) ABSTRACT

Disclosed is an exhaust gas analyzing system which includes a main flow passage provided with a PM collection filter, a diluted exhaust gas sampling flow passage connected upstream of the PM collection filter of the main flow passage for sampling a part of diluted exhaust gas, a diluted exhaust gas flow rate adjusting mechanism connected downstream of the PM collection filter of the main flow passage, and control equipment altering a setting flow rate of the diluted exhaust gas flow rate adjusting mechanism depending on a flow rate of sampling diluted exhaust gas flowing through the diluted exhaust gas sampling flow passage.

9 Claims, 3 Drawing Sheets

(56) References Cited

FOREIGN PATENT DOCUMENTS

| | | | |
|---|---|---|---|
| CN | 103969088 | A | 8/2014 |
| EP | 2302354 | A1 | 3/2011 |
| EP | 2515095 | A1 | 10/2012 |
| JP | 01-117748 | U1 | 8/1989 |
| JP | 2000-028499 | A | 1/2000 |
| JP | 2001-264223 | A | 9/2001 |
| JP | 2003-050194 | A | 2/2003 |
| JP | 2012-026892 | A | 2/2012 |
| WO | 2010007965 | A1 | 1/2010 |

OTHER PUBLICATIONS

Office Action dated Sep. 20, 2018 issued for Japanese Patent Application No. 2014-218275, 6 pgs.

Office Action dated Feb. 28, 2019 issued for Chinese Patent Application No. 201510690762.3, 15 pgs.

EXHAUST GAS ANALYZING SYSTEM AND PUMPING DEVICE

CROSS-REFERENCE TO RELATED APPLICATION

This application claims priority to JP Application No. 2014-218275, filed Oct. 27, 2014, the disclosure of which is incorporated in its entirety by reference herein.

BACKGROUND OF THE INVENTION

1. Field of the Invention

The present disclosure relates to an exhaust gas analyzing system for sampling a part of or a whole of exhaust gas, emitted from an internal combustion engine, which is diluted and analyzed. Further, the present disclosure relates to a pumping device preferably used in the exhaust gas analyzing system.

2. Description of the Related Art

In the related art, a measuring system for particulate matters (PM), contained in exhaust gas, has been proposed including, as shown in WO2010/007965A, a combination of PM collection, employing a PM collection filter, and continuous measurement for measuring a particulate diameter concentration or the like upon using an analyzer such as a diffusion charge sensor (DCS).

More particularly, such a measuring system allows an exhaust gas introduction pipe to divert and sample a part of exhaust gas, emitted from the internal combustion engine, which is introduced into a micro tunnel (a diluter) for dilution with dilution gas. Then, the measuring system causes diluted exhaust gas, diluted in the micro tunnel, to be introduced into the PM collection filter. Moreover, the measuring system has a diluted exhaust gas sampling pipe for sampling a part of diluted exhaust gas at an upstream side of the PM collection filter for introduction to the analyzer such as the diffusion charge sensor (DCS).

Here, the measuring system has a flow rate adjusting mechanism, such as an electromagnetic proportional valve, which is disposed in a dilution gas introduction pipe connected to the micro tunnel. Such measuring system controls the flow rate adjusting mechanism to perform diverting dilution control on the basis of a flow rate of exhaust gas emitted from the internal combustion engine. That is, the measuring system adjusts the flow rate of dilution gas to be introduced into the micro tunnel such that a ratio (diverting ratio) between the flow rate of exhaust gas, emitted from the internal combustion engine, and the flow rate of exhaust gas diverted and sampled by the exhaust gas introduction pipe becomes constant.

With the measuring system performing such diverting dilution control, the flow rate of diluted exhaust gas, sampled by the diluted exhaust gas sampling pipe, results in the occurrence of an error in performing diverting dilution control with degradation occurring in analysis precision. For this reason, the measuring system is configured to allow correction gas (for instance, air) to be returned to a downstream side of the PM collection filter at the same flow rate as the sampling flow rate of the diluted exhaust gas sampling pipe. More particularly, a correction gas introduction pipe is connected between the PM collection filter and a suction pump provided at the downstream side of the PM collection filter. The correction gas introduction pipe has a mass flow controller provided for controlling the flow rate of correction gas at the same flow rate as the sampling flow rate.

However, in order for correction gas to flow into the downstream side of the PM collection filter via the mass flow controller, a compressed air source (compressor) needs to be provided at an upstream side of the mass flow controller. This results in the occurrence of an issue with a difficulty in downsizing the measuring system.

SUMMARY OF THE INVENTION

Problems to be Solved by the Invention

The present invention has been completed with a view to addressing the above issues and has an object to eliminate the need of the correction gas introduction pipe having the compressed air source while suppressing the occurrence of degradation in analysis precision of exhaust gas.

That is, one aspect of the present invention provides an exhaust gas analyzing system for sampling a part of or a whole of an exhaust gas emitted from an internal combustion engine, diluting the exhaust gas for analysis, and analyzing the resulting gas, the system including: an exhaust gas flow passage through which the exhaust gas flows; a dilution gas flow passage through which dilution gas flows; a main flow passage connected to the exhaust gas flow passage and to the dilution gas flow passage, that flows a diluted exhaust gas resulting from mixing the exhaust gas and the dilution gas with each other, and which is provided with a first analyzing equipment for analyzing the exhaust gas; a diluted exhaust gas sampling flow passage connected to the main flow passage at an upstream side of the first analyzing equipment for sampling a part of the diluted exhaust gas from the main flow passage for introduction to a second analyzing equipment for analyzing the exhaust gas; a diluted exhaust gas flow rate adjusting mechanism connected to the main flow passage at a downstream side of the first analyzing equipment that adjusts a flow rate of the diluted exhaust gas flowing through the main flow passage; and a control equipment that alters a setting flow rate of the diluted exhaust gas flow rate adjusting mechanism on the basis of a sampling flow rate of the diluted exhaust gas flowing through the diluted exhaust gas sampling flow passage.

Such a configuration alters the setting flow rate of the diluted exhaust gas flow rate adjusting mechanism on the basis of the sampling flow rate of diluted exhaust gas flowing through the diluted exhaust gas sampling flow passage. Thus, it becomes possible to eliminate the need of the correction gas flow passage having the compressed air source while preventing the fluctuations of the total flow rate of the flow rate of exhaust gas, flowing through the exhaust gas flow passage, and the flow rate of dilution gas, flowing through the dilution gas flow passage, depending on the sampling flow rate. This enables the exhaust gas analyzing system to be downsized while suppressing the degradation in analysis precision.

If no attempt is made during diverting dilution control, to alter the setting flow rate of the diluted exhaust gas flow rate adjusting mechanism depending on the flow rate of sampling diluted exhaust gas, the total flow rate (the flow rate of dilution gas appearing at the upstream side of the diluted exhaust gas sampling flow passage) fluctuates depending on the flow rate of sampling diluted exhaust gas. As a result, an error tends to occur in diverting dilution control.

To eliminate such an error in diverting dilution control, in particular, the exhaust gas analyzing system may further preferably including: a dilution gas flow rate adjusting mechanism provided in the dilution gas flow passage for adjusting a flow rate of the dilution gas flowing through the dilution gas flow passage, the control equipment controlling the diluted exhaust gas flow rate adjusting mechanism and the dilution gas flow rate adjusting mechanism for increasing or decreasing the flow rate of the dilution gas such that a total flow rate, of the flow rate of the exhaust gas flowing through the exhaust gas flow passage and the flow rate of the dilution gas flowing through the dilution gas flow passage, is adjusted to a predetermined flow rate, and such that the flow rate of the exhaust gas flowing through the exhaust gas flow passage is adjusted to a predetermined ratio with respect to the flow rate of the exhaust gas emitted from the internal combustion engine, and the control equipment determining the setting flow rate of the diluted exhaust gas flow rate adjusting mechanism, to a value that results from subtracting the sampling flow rate of the diluted exhaust gas from the total flow rate.

It is preferable that the diluted exhaust gas flow rate adjusting mechanism include a suction pump, and that the controlling equipment control the revolution speed of the suction pump, and therefore establish the setting flow rate of the diluted exhaust gas.

With such a configuration, there is only a need to control the revolution speed of the suction pump, enabling the simplification of a device structure.

The diluted exhaust gas flow rate adjusting mechanism may preferably include: a suction pump; a circulation flow passage connected to an inlet side and an outlet side of the suction pump for circulating a part of the diluted exhaust gas from the outlet side of the suction pump to the inlet side; and a circulation flow rate adjusting mechanism disposed in the circulation flow passage for adjusting a circulation flow rate of the diluted exhaust gas, the controlling equipment controlling the circulation flow rate in the circulation flow passage by controlling the circulation flow rate adjusting mechanism, and therefore establishing the setting flow rate of the diluted exhaust gas.

Thus, merely controlling the circulation flow rate adjusting mechanism, disposed in the circulation flow passage, enables the setting flow rate to lie at a desired value while rotating the pump at a high speed of the order that can cancel the fluctuations of the pump. Further, no need arises for a flow rate adjusting mechanism (for instance, a proportional valve) to be disposed at the inlet side or the outlet side of the pump for adjusting the flow rate. Thus, the pump can work to the limit of its capability to draw a negative pressure fluid without taking a pressure loss of the flow rate adjusting mechanism into consideration.

Furthermore, even if the flow rate passing through the PM collection filter is reduced due to clogging of the PM collection filter during an exhaust gas analyzing period, it is possible to compensate the reduced amount of the flow rate by controlling the circulation flow rate adjusting mechanism without necessity of changing the revolution speed of the pump.

The first analyzing equipment may preferably include a PM collection filter for collecting particulate matter contained in the diluted exhaust gas, and the second analyzing equipment may preferably include an analyzer that continuously measures particulate matter contained in the diluted exhaust gas. Examples of the analyzer may conceivably include those which can continuously measure physical property such as a surface area, the number and particulate size distribution of the particulate matter, which indirectly indicates a mass of the particulate matter.

With this configuration, it is possible to determine dynamic change of the mass of the particulate matter, by correlating the mass of the particulate matter obtained by the PM collection filter and a measurement value obtained by the analyzer.

The exhaust gas analyzing system may be preferably installed onto an actual vehicle capable of traveling on a road, for measuring particulate matter in exhaust gas during traveling of the vehicle. With such an arrangement, the effect of the present invention can be remarkably exhibited.

Further, another aspect of the present invention provides a pumping device including: a flow passage having an inflow port and an outflow port; a pump disposed in the flow passage; a circulation flow passage connecting an inlet side and an outlet side of the pump to each other to circulate a part of a fluid from the outlet side of the pump to the inlet side; and a circulation flow rate adjusting mechanism disposed in the circulation flow passage for adjusting a circulation flow rate of the fluid. The circulation flow rate adjusting mechanism adjusts the circulation flow rate in the circulation flow passage, and therefore adjusts the flow rate of the fluid flowing into the inflow port or the flow rate of the fluid discharging from the outflow port. With such a configuration, permitting the circulation flow rate adjusting mechanism to regulate the circulation flow rate enables the pumping device to control the flow rate while keeping the revolution speed of the pump in a fixed rotation. In addition, adjusting the circulation flow rate with the pump remained to be variable in rotation enables the pumping device to have an increased freedom of controlling the flow rate.

Effect of the Invention

With the present invention of such a configuration, the correction gas introduction pipe, having the compressed air source, can be dispensed with while suppressing the degradation of analysis precision of exhaust gas.

DETAILED DESCRIPTION OF THE PREFERRED EMBODIMENTS

Now, an exhaust gas analyzing system of one embodiment according to the present invention is described with reference to the accompanying drawings.

The exhaust gas analyzing system 100 of the present embodiment is installed on an automobile such as a passenger car and a truck and serves to measure a mass concentration of particulate matters (PM) contained in exhaust gas emitted from an engine in the form of an internal combustion engine during traveling on a road.

Figure 1:
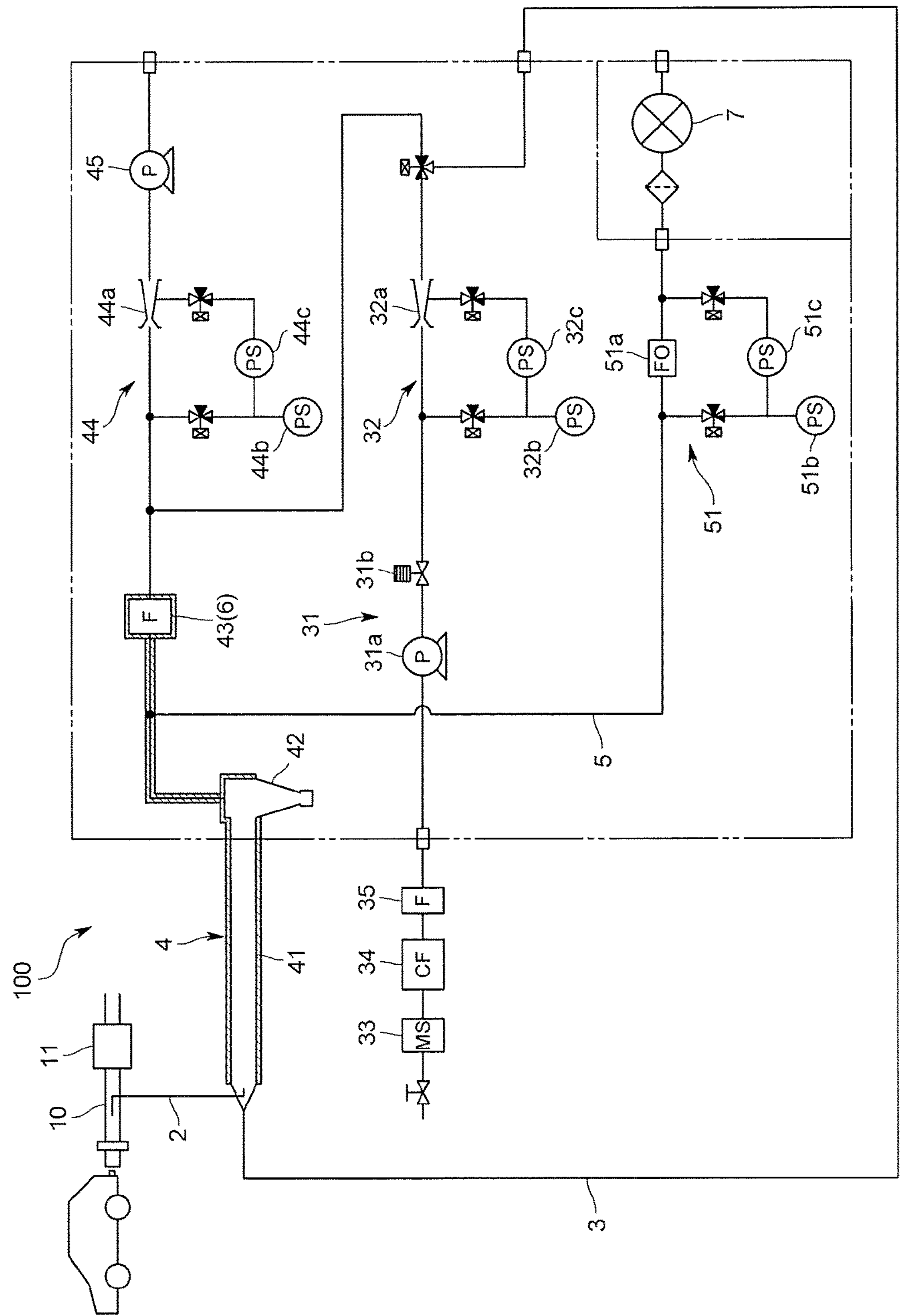
FIG. 1 is a typical view illustrating a structure of an exhaust gas analyzing system of an embodiment according to the present invention.

As shown in FIG. 1, more particularly, the exhaust gas analyzing system 100 is configured to divert and sample a part of exhaust gas, flowing through an exhaust pipe connected to the engine, for diluting the resulting exhaust gas for analysis. The system 100 includes: an exhaust gas flow passage 2 through which exhaust gas flows; a dilution gas flow passage 3 through which dilution gas flows; a main flow passage 4 to which the exhaust gas flow passage 2 and the dilution gas flow passage 3 are connected to flow diluted exhaust gas resulting from mixing exhaust gas and dilution gas; and a diluted exhaust gas sampling flow passage 5 sampling a part of diluted exhaust gas from the main flow passage 4.

Hereinafter, the respective flow passages 2 to 5 and associated equipments, disposed in the flow passages 2 to 5, will be described.

The exhaust gas flow passage 2 serves to divert and sample the part of exhaust gas, flowing through the exhaust pipe or an attachment pipe 10 covering an opening of the exhaust pipe, and to introduce the same to the main flow passage 4 without dilution being performed. The exhaust gas flow passage 2 has one end extending to the inside of the exhaust pipe or the attachment pipe 10 and the other end connected to the main flow passage 4. In the present embodiment, the exhaust gas flow passage 2 has no provision of measuring equipment for measuring an exhaust gas flow rate and control equipment for controlling the exhaust gas flow rate.

Further, an exhaust gas flow sensor 11 such as a pitot tube type flow sensor is disposed in the exhaust pipe or the attachment pipe 10 at a position downstream of the one end opening of the exhaust gas flow passage 2. The exhaust gas flow sensor 11 measures the flow rate of exhaust gas flowing through the exhaust pipe or the attachment pipe 10, i.e., the flow rate of exhaust gas flowing out of the internal combustion engine.

The dilution gas flow passage 3, used for introducing dilution gas (atmospheric air in the present embodiment) into the main flow passage 4 for diluting exhaust gas, has one end, placed at a position capable of taking in atmospheric air, and the other end connected to the main flow passage 4. Furthermore, the dilution gas flow passage 3 has a dilution gas flow rate adjusting mechanism 31 for adjusting a flow rate of dilution gas introduced into the main flow passage 4 and a dilution gas flow rate measuring mechanism 32 for measuring the flow rate of relevant dilution gas, both of which are located from an upstream side in this order.

In a position upstream of the dilution gas flow rate adjusting mechanism 31, moreover, the dilution gas flow passage 3 has a mist separator 33 for removing moisture contained in atmospheric air, a filter 34 such as an activated carbon adsorption filter for removing organic constituents contained in atmospheric air, and a filter 35 such as a HEPA filter for removing dust contained in atmospheric air. These components are located from the upstream side in this order.

The dilution gas flow rate adjusting mechanism 31 includes a supply pump 31*a* of, for instance, a diaphragm type and a flow rate control valve 31*b* such as an electromagnetic proportional valve disposed at a position upstream or downstream (at a downstream side in the present embodiment) of the supply pump 31*a*. In addition, the dilution gas flow rate measuring mechanism 32 is of a differential pressure type and includes a venturi 32*a*, a pressure sensor 32*b* for measuring an inlet pressure of the venturi 32*a* and a differential pressure sensor 32*c* for measuring a differential pressure between an inlet and a throat portion of the venturi 32*a*. Moreover, such a structure may be of the type that includes, other than the venturi 32*a*, a fluid resistor such as an orifice, a flow nozzle and a pitot tube.

On the basis of a dilution gas flow rate obtained by the dilution gas flow rate measuring mechanism 32 of such a structure, a valve opening of the flow rate control valve 31*b* of the dilution gas flow rate adjusting mechanism 31 is controlled by control equipment, not shown in the drawings, thereby controlling the flow rate of dilution gas introduced into the main flow passage 4.

The main flow passage 4 includes: a diluter (micro tunnel) 41 to which the exhaust gas flow passage 2 and the dilution gas flow passage 3 are connected to mix exhaust gas and dilution gas with each other; a dust remover 42 of, for instance, a cyclone type disposed downstream of the diluter 41 for removing dust from diluted exhaust gas; a filter installed portion 43 disposed downstream of the dust remover 42 at which a PM collection filter 6, serving as a first analyzing equipment, is disposed; a diluted exhaust gas flow rate measuring mechanism 44 disposed downstream of the filter installed portion 43 (PM collection filter 6) for measuring the flow rate of diluted exhaust gas passing through the main flow passage 4; and a diluted exhaust gas flow rate adjusting mechanism 45, disposed downstream of the diluted exhaust gas flow rate measuring mechanism 44, for adjusting the flow rate of diluted exhaust gas. The diluter 41, the dust remover 42, the filter installed portion 43 and associated flow channels are heated by a heater at a predetermined temperature (of, for instance, 47±5° C.).

The diluted exhaust gas flow rate measuring mechanism 44 is of a differential pressure type and includes a venturi 44*a*, a pressure sensor 44*b* for measuring a pressure at an inlet of the venturi 44*a*, and a differential pressure sensor 44*c* for measuring a differential pressure between the inlet and a throat portion of the venturi 44*a*. Moreover, such a structure may be of the type that includes, other than the venturi 44*a*, a fluid resistor such as an orifice, a flow nozzle and a pitot tube.

Further, the diluted exhaust gas flow rate adjusting mechanism 45, including a suction pump of, for instance, a diaphragm type, has control equipment, not shown in the drawings, which is configured to control the revolution speed of the pump such that a suction flow rate can be altered. Furthermore, the suction pump is structured such that a suction flow rate at an inlet side and a discharge flow rate at an outlet side are equal to each other.

The diluted exhaust gas sampling flow passage 5, serving to sample the part of diluted exhaust gas from the main flow passage 4 for introduction to an analyzer 7 in the form of a second analyzing equipment, includes a sampling flow rate measuring mechanism 51 for measuring a sampling flow rate of diluted exhaust gas flowing through the diluted exhaust gas sampling flow passage 5. With the present embodiment, the suction pump (not shown), incorporated inside the analyzer 7, is configured to allow the diluted exhaust gas sampling flow passage 5 to collect diluted exhaust gas. However, the suction pump may be disposed downstream of the sampling flow rate measuring mechanism 51 to be separate from the analyzer 7. In addition, the analyzer 7, used for continuously measuring the particulate matters contained in diluted exhaust gas, serves to continuously measure physical properties such as, for instance, a surface area, the number and a particle size distribution or the like indirectly indicating a mass of particulate matters. Examples of the analyzer of the present embodiment may include a diffusion charging sensor (DSC), a hydrogen flame ionization detector (FID), a condensation particle counter (CPC), an electrical low pressure impactor (ELPI) and a scanning mobility particle sizer (SMPS), etc.

The sampling flow rate measuring mechanism 51 is of a differential pressure type and includes an orifice 51*a*, a pressure sensor 51*b* for measuring an upstream pressure of the orifice 51*a*, and a differential pressure sensor 51*c* for measuring a differential pressure between the upstream and a downstream of the orifice 51*a*. Moreover, such a structure may be of the type that includes, other than the orifice 51*a*, a fluid resistor such as a venturi, a flow nozzle and a pitot tube.

Further, control equipment of the exhaust gas analyzing system 100 controls the dilution gas flow rate adjusting mechanism 31 and the diluted exhaust gas flow rate adjusting mechanism 45 for thereby performing control (diverting dilution control) of the flow rate of dilution gas, introduced into the diluter 41, on a real time basis. This allows a ratio (diverting ratio) between the exhaust gas discharge flow rate, obtained by the exhaust gas flow rate sensor 11, and the exhaust gas flow rate, flowing through the exhaust gas flow passage 2, to become constant.

Figure 2:
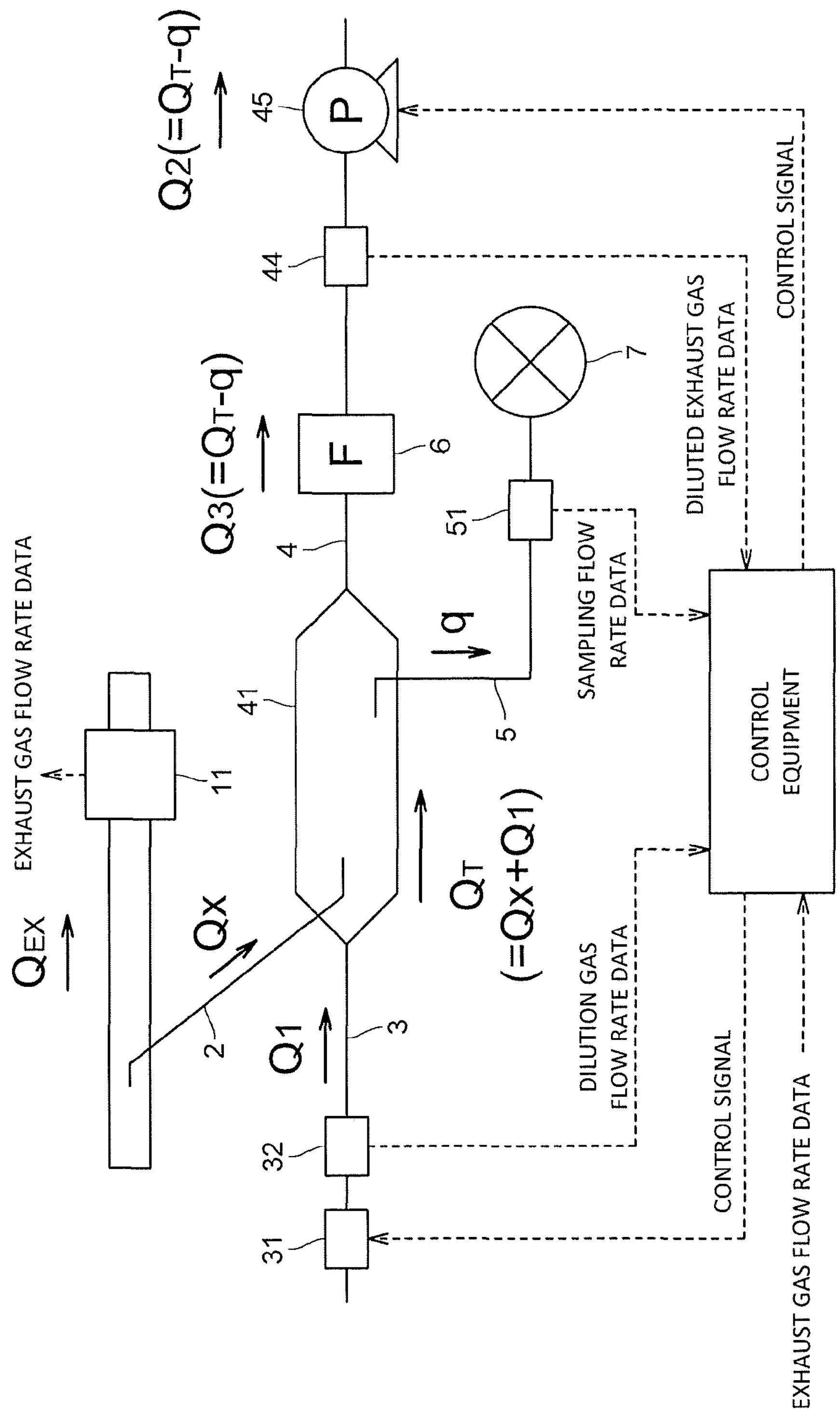
FIG. 2 is a typical view showing a flow rate of fluids flowing through respective flow passages.

As shown in FIG. 2, more particularly, control equipment allows the flow rate $Q_x$ (diverting flow rate) of exhaust gas, flowing through the exhaust gas flow passage 2, and the total flow rate $Q_T(=Q_x+Q_1)$ of the flow rate $Q_1$ of dilution gas, flowing through the dilution gas flow passage 3, to become constant. The flow rate $Q_1$ of dilution gas is increased or decreased such that an exhaust gas discharge flow rate $Q_{EX}$ and the diverting flow rate $Q_x$ fall at a fixed ratio. That is, control equipment acquires exhaust-gas discharge flow-rate data from the exhaust gas flow sensor 11 and inputs a control signal, based on resulting exhaust-gas discharge flow-rate data, to the electromagnetic proportional valve 31*b* of the dilution gas flow rate adjusting mechanism 31 such that the flow rate $Q_1$ of dilution gas is increased or decreased.

Further, control equipment allows the diluted exhaust gas flow rate adjusting mechanism 45 to alter the setting flow rate $Q_2$ depending on the sampling flow rate q of diluted exhaust gas flowing through the diluted exhaust gas sampling flow passage 5. That is, control equipment acquires sampling flow rate data from the sampling flow rate measuring mechanism 51 and inputs a control signal, based on resulting sampling flow rate data, to the diluted exhaust gas flow rate adjusting mechanism 45 such that the setting flow rate $Q_2$ is altered.

In the absence of the diluted exhaust gas sampling flow passage 5 in the system, the setting flow rate $Q_2$ becomes the total flow rate $Q_T$ and matches the flow rate $Q_3$ of diluted exhaust gas passing through the PM collection filter 6.

More particularly, control equipment allows the setting flow rate $Q_2$ to be equal to a value $(Q_T-q)$ resulting from subtracting the sampling flow rate q from the total flow rate $Q_T$. Thus, the total flow rate $Q_T$ (that is, the flow rate of diluted exhaust gas prevailing at a position upstream of the one end opening of the diluted exhaust gas sampling flow passage 5) can be maintained at a set value (constant value) regardless of the sampling flow rate q of the diluted exhaust gas sampling flow passage 5. When this takes place, the filtering flow rate $Q_3$ of the PM collection filter takes the value $(Q_T-q)$ resulting from subtracting the sampling flow rate q from the total flow rate $Q_T$.

Since the diluted exhaust gas flow rate adjusting mechanism 45 of the present embodiment includes the suction pump that is variable in revolution speed, control equipment controls the number of revolutions of the suction pump depending on the sampling flow rate q of diluted exhaust gas flowing through the diluted exhaust gas sampling flow passage 5 to establish the setting flow rate $Q_2(=Q_T-q)$.

With the exhaust gas analyzing system 100, continuously measured data (for instance, continuous particle size concentration data), acquired by the analyzer, is stored during a period in which diluted exhaust gas is collected by the PM collection filter 6. After the completion of sampling data, calculation is made to acquire a ratio between a particle size concentration integrated value obtained only for an interval, in which effective data is acquired, and an integrated value of a particle size concentration obtained for a whole interval. In this instance, assuming that there is a correlation between a concentration value, obtained by the analyzer, and a mass of PM, using such a ratio makes it possible to calculate the mass of PM only for an effective interval based on the mass of collected PM for the whole interval obtained in a filtering weight method.

With the exhaust gas analyzing system 100 of such a structure, the diluted exhaust gas flow rate adjusting mechanism 45 alters the setting flow rate $Q_2$ depending on the sampling flow rate q of diluted exhaust gas flowing through the diluted exhaust gas sampling flow passage 5. This prevents fluctuations in the total flow rate $Q_T(=Q_x+Q_1)$ of the flow rate $Q_x$ of exhaust gas flowing through the exhaust gas flow passage 2, and the flow rate $Q_1$ of dilution gas flowing through the dilution gas flow passage 3 according to the sampling flow rate q, thereby eliminating the need of the correction gas flow passage having the compressed air source. Thus, the exhaust gas analyzing system 100 can be miniaturized while suppressing an error in diverting dilution control to avoid the degradation in analysis precision.

Further, there is no likelihood that diluted exhaust gas, passing through the PM collection filter 6, is mixed with gas (for instance, correction gas or atmospheric air in the related art) admitted from the outside. Thus, it is possible to measure, for instance, a $CO_2$ concentration, etc., of diluted exhaust gas by using an exhaust (particularly at a position downstream of the diluted exhaust gas flow rate adjusting mechanism 45) in the main flow passage 4, enabling the precision of a dilution ratio to be easily verified.

The present invention is not limited to the embodiment described above.

Figure 3:
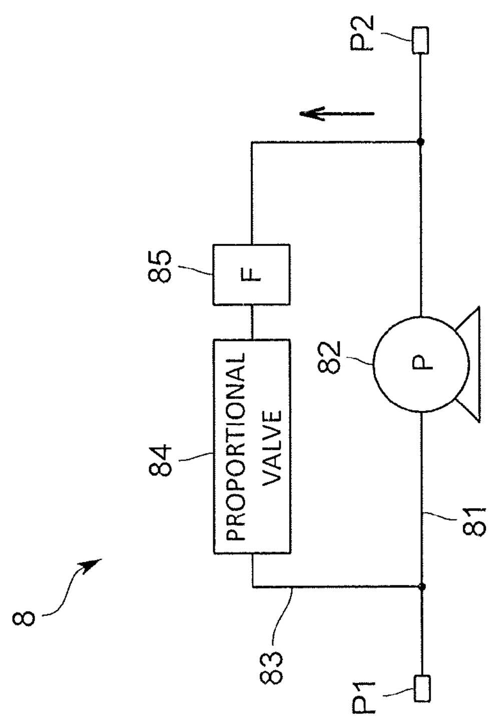
FIG. 3 is a typical view showing a diluted exhaust gas flow rate adjusting mechanism (pumping device) of a modified form of the present embodiment.

For instance, the diluted exhaust gas flow rate adjusting mechanism of the above embodiment, configured to include the suction pump of the variable speed, may also be configured to include a pumping device 8 shown in FIG. 3.

The pumping device 8 includes a flow passage 81 having an inflow port P1 and an outflow port P2, a pump 82 disposed in the flow passage 81, a circulation flow passage 83 connected to an inlet side and an outlet side of the pump 82 for circulating a part of diluted exhaust gas from the outlet side to the inlet side of the pump 82, and a circulation flow rate adjusting mechanism 84 disposed in the circulation flow passage 83 to regulate a flow rate of circulating diluted exhaust gas.

The pump 82 is configured such that a suction flow rate at an inlet side and a discharge flow rate at an outlet side are equal to each other in the flow passage 81. Further, the circulation flow rate adjusting mechanism 84 includes an electromagnetic proportional valve that has a valve opening controlled by control equipment depending on the sampling flow rate of the diluted exhaust gas sampling flow passage 5. In FIG. 3, furthermore, a dustproof filter 85 is disposed in the circulation flow passage 83 at an upstream side of the circulation flow rate adjusting mechanism 84.

With control equipment controlling the circulation flow rate adjusting mechanism 84, the circulating flow rate of diluted exhaust gas, flowing through the circulation flow passage 83, is regulated for adjusting the flow rate of diluted exhaust gas entering from the inflow port P1 or the flow rate of diluted exhaust gas flowing out of the outflow port P2.

With such a pumping device 8, merely controlling the circulation flow rate adjusting mechanism 84 enables the setting flow rate to be set to a desired value. Further, the pump 82 can be fixed to, for instance, a rated revolution speed and a high speed revolution speed of the order capable of disregarding the occurrence of fluctuations. Furthermore, no need arises for a flow rate adjusting mechanism to be disposed at the inlet side or the outlet side of the pump 82 for regulating the flow rate. This enables the pump 82 to operate to the limit of own ability for drawing fluid under a negative pressure without taking a pressure loss of the flow rate adjusting mechanism into consideration. In addition, it is configured such that diluted exhaust gas per se is circulated with no occurrence of mixing with other gas. This allows the flow rate of the inflow port P1 and the flow rate of the outflow port P2 of the pumping device 8 to be equal to each other. Therefore, this makes it possible to locate the flow rate measuring mechanism in any of the upstream side and the downstream side of the pumping device 8, thereby allowing the analyzer to be connected to the downstream side of the pumping device 8 for analyzing diluted exhaust gas.

Further, due to the clogging of the PM collection filter during exhaust gas analysis, there is a possibility of degradation occurring in the filtering flow rate of diluted exhaust gas passing through the PM collection filter, resulting in a need to vary the revolution speed of the pump 82. In general, as the revolution speed of the pump 82 is decreased, fluctuations are caused to occur. In such case, without varying the revolution speed of the pump 82, it is possible to cancel a reduction in the filtering flow rate due to the clogging while suppressing the fluctuations by controlling the circulation flow rate adjusting mechanism 84 to compensate the reduction in the filtering flow rate.

With the embodiment set forth above, proportional dilution control is performed to control the flow rate of dilution gas introduced into the main flow passage such that the exhaust gas is diverted and sampled at a fixed ratio with respect to the flow rate of the exhaust gas emitted from the internal combustion engine, and is introduced into the main flow passage. However, fixed dilution control may be performed to control the flow rate of dilution gas so as to make a dilution ratio to be constant, i.e., to make a ratio between the diverting flow rate of the exhaust gas diverted and sampled through the exhaust gas flow passage, and the flow rate of dilution gas to be constant.

Furthermore, while the embodiment set forth above is configured to divert and sample the part of exhaust gas emitted from the internal combustion engine, it may be configured that the whole of exhaust gas is collected and the collected exhaust gas is subjected to dilution and analysis.

Moreover, the exhaust gas analyzing system of the embodiment may be arranged to collect a part of or a whole of exhaust gas emitted from an engine of an automobile placed on a chassis dynamometer and dilute the collected exhaust gas for analysis.

In addition, while the embodiment is configured to analyze exhaust gas emitted from the internal combustion engine installed on the automobile, another alternative may be adopted to analyze exhaust gas emitted from an internal combustion engine installed on other moving object such as an air plane, a ship or the like.

Besides, it is needless to say that the present invention is not limited to the embodiments set forth above and various modifications may be made without departing from the scope of the present invention.

DESCRIPTION OF REFERENCE NUMERALS

100 exhaust gas analyzing system
2 exhaust gas flow passage
3 dilution gas flow passage
31 dilution gas flow rate adjusting mechanism
32 dilution gas flow rate measuring mechanism
4 main flow passage
44 diluted exhaust gas flow rate measuring mechanism
45 diluted exhaust gas flow rate adjusting mechanism (suction pump)
5 diluted exhaust gas sampling flow passage
51 sampling flow rate measuring mechanism
6 first analyzing equipment (PM collection filter)
7 second analyzing equipment (analyzer)
8 pumping device
82 pump
83 circulation flow passage
84 circulation flow rate adjusting mechanism

What is claimed is:

1. An exhaust gas analyzing system for sampling a part of or a whole of an exhaust gas emitted from an internal combustion engine, diluting the exhaust gas for analysis, and analyzing resulting gas, the system comprising:
- an exhaust gas flow passage through which the exhaust gas flows;
- a dilution gas flow passage through which dilution gas flows;
- a main flow passage, provided with a PM collection filter and connected to the exhaust gas flow passage and to the dilution gas flow passage, that flows a diluted exhaust gas resulting from mixing the exhaust gas and the dilution gas with each other;
- a diluted exhaust gas sampling flow passage connected to the main flow passage at an upstream side of the PM collection filter for sampling a part of the diluted exhaust gas from the main flow passage for introduction to an exhaust gas analyzer that continuously measures particulate matter contained in the diluted exhaust gas;
- a diluted exhaust gas flow rate adjusting mechanism connected to the main flow passage at a downstream side of the PM collection filter that adjusts a flow rate of the diluted exhaust gas flowing through the main flow passage; and
- a controller that alters a setting flow rate of the diluted exhaust gas flow rate adjusting mechanism on a basis of a sampling flow rate of the diluted exhaust gas flowing through the diluted exhaust gas sampling flow passage.

2. The exhaust gas analyzing system according to claim 1, wherein the diluted exhaust gas flow rate adjusting mechanism comprises a suction pump, the controller controlling a revolution speed of the suction pump to establish the setting flow rate of the diluted exhaust gas.

3. The exhaust gas analyzing system according to claim 1, wherein the diluted exhaust gas flow rate adjusting mechanism comprise a suction pump, and a circulation flow passage connected to an inlet side and an outlet side of the suction pump for circulating a part of the diluted exhaust gas from the outlet side to the inlet side, the controller controlling a circulation flow rate of the diluted exhaust gas in the circulation flow passage to establish the setting flow rate of the diluted exhaust gas.

4. The exhaust gas analyzing system according to claim 1, being installed onto a vehicle capable of traveling on a road, for measuring particulate matter in exhaust gas during traveling of the vehicle.

5. An exhaust gas analysis method using an exhaust gas analyzing system for sampling a part of or a whole of an exhaust gas emitted from an internal combustion engine, diluting the exhaust gas for analysis, and analyzing resulting gas, the exhaust gas analyzing system including an exhaust gas flow passage through which the exhaust gas flows, a dilution gas flow passage through which dilution gas flows, a main flow passage, provided with a PM collection filter and connected to the exhaust gas flow passage and to the dilution gas flow passage, that flows a diluted exhaust gas resulting from mixing the exhaust gas and the dilution gas with each other, a diluted exhaust gas sampling flow passage connected to the main flow passage at an upstream side of the PM collection filter for sampling a part of the diluted exhaust gas from the main flow passage for introduction to an exhaust gas analyzer that continuously measures particulate matter contained in the diluted exhaust gas, and a diluted exhaust gas flow rate adjusting mechanism connected to the main flow passage at a downstream side of the PM collection filter that adjusts a flow rate of the diluted exhaust gas flowing through the main flow passage, the method comprising:

altering a setting flow rate of the diluted exhaust gas flow rate adjusting mechanism on a basis of a sampling flow rate of the diluted exhaust gas flowing through the diluted exhaust gas sampling flow passage.

6. An exhaust gas analyzing system for sampling a part of or a whole of an exhaust gas emitted from an internal combustion engine, diluting the exhaust gas for analysis, and analyzing resulting gas, the system comprising:

an exhaust gas flow passage through which the exhaust gas flows;

a dilution gas flow passage through which dilution gas flows;

a main flow passage, provided with a PM collection filter and connected to the exhaust gas flow passage and to the dilution gas flow passage, that flows a diluted exhaust gas resulting from mixing the exhaust gas and the dilution gas with each other;

a diluted exhaust gas sampling flow passage connected to the main flow passage at an upstream side of the PM collection filer for sampling a part of the diluted exhaust gas from the main flow passage for introduction to an exhaust gas analyzer;

a diluted exhaust gas flow rate adjusting mechanism connected to the main flow passage at a downstream side of the PM collection filter that adjusts a flow rate of the diluted exhaust gas flowing through the main flow passage; and a controller that alter a setting flow rate of the diluted exhaust gas flow rate adjusting mechanism on a basis of a sampling flow rate of the diluted exhaust gas flowing through the diluted exhaust gas sampling flow passage, and adjusts the flow rate of the dilution gas flowing through the dilution gas flow passage such that a total flow rate, of the flow rate of the exhaust gas flowing through the exhaust gas flow passage and the flow rate of the dilution gas flowing through the dilution gas flow passage, is adjusted to a predetermined flow rate, and such that the flow rate of the exhaust gas flowing through the exhaust gas flow passage is adjusted to a predetermined ratio with respect to the flow rate of the exhaust gas emitted from the internal combustion engine, the flow rate of the diluted exhaust gas flowing through the main flow passage at the downstream side of the PM collection filter being adjusted to a value that results from subtracting the sampling flow rate of the diluted exhaust gas from the total flow rate.

7. The exhaust gas analyzing system according to claim 6, wherein the diluted exhaust gas flow rate adjusting mechanism comprises a suction pump, the controller controlling a revolution speed of the suction pump to establish the setting flow rate of the diluted exhaust gas.

8. The exhaust gas analyzing system according to claim 6, wherein the diluted exhaust gas flow rate adjusting mechanism comprises a suction pump, and a circulation flow passage connected to an inlet side and an outlet side of the suction pump for circulating a part of the diluted exhaust gas from the outlet side to the inlet side, the controller controlling a circulation flow rate of the diluted exhaust gas in the circulation flow passage to establish the setting flow rate of the diluted exhaust gas.

9. The exhaust gas analyzing system according to claim 6, being installed onto a vehicle capable of traveling on a road, for measuring particulate matter in exhaust gas during traveling of the vehicle.

* * * * *